US009747743B2

(12) United States Patent
Brown

(10) Patent No.: US 9,747,743 B2
(45) Date of Patent: Aug. 29, 2017

(54) PATIENT-SPECIFIC MEDICATION DISPENSING AND NOTIFICATION SYSTEM

(75) Inventor: Barry Arthur Brown, Encinitas, CA (US)

(73) Assignee: CAREFUSION 303, INC., San Diego, CA (US)

( * ) Notice: Subject to any disclaimer, the term of this patent is extended or adjusted under 35 U.S.C. 154(b) by 319 days.

(21) Appl. No.: 11/833,869

(22) Filed: Aug. 3, 2007

(65) Prior Publication Data

US 2009/0037020 A1    Feb. 5, 2009

(51) Int. Cl.
*G06F 19/00* (2011.01)
*G07F 17/00* (2006.01)
*G07F 11/62* (2006.01)
*A61G 12/00* (2006.01)

(52) U.S. Cl.
CPC ...... *G07F 17/0092* (2013.01); *G06F 19/3462* (2013.01); *G07F 11/62* (2013.01); *A61G 12/001* (2013.01)

(58) Field of Classification Search
CPC ... G07F 11/62; G07F 17/0092; A61G 12/001; G06F 19/3462
USPC .................................................. 700/231–244
See application file for complete search history.

(56) References Cited

U.S. PATENT DOCUMENTS

| | | | | |
|---|---|---|---|---|
| 6,032,155 | A * | 2/2000 | de la Huerga | 707/104.1 |
| 6,219,587 | B1 * | 4/2001 | Ahlin et al. | 700/233 |
| 6,604,019 | B2 * | 8/2003 | Ahlin et al. | 700/231 |
| 6,636,780 | B1 * | 10/2003 | Haitin | A61G 12/001 221/2 |
| 6,876,902 | B2 * | 4/2005 | Nikolich | 700/242 |
| 7,155,306 | B2 * | 12/2006 | Haitin | A61G 12/001 700/242 |
| 7,216,802 | B1 | 5/2007 | De La Huerga | |

(Continued)

FOREIGN PATENT DOCUMENTS

CN         1397901 A      2/2003
WO    WO 2006/060572 A1   6/2006

OTHER PUBLICATIONS

International Search Report/Written Opinion PCT/US2008/071998, mailed May 7, 2008.

(Continued)

*Primary Examiner* — Michael K Collins
(74) *Attorney, Agent, or Firm* — McDermott Will & Emery LLP

(57) ABSTRACT

A medication dispensing system is described. In some embodiments, the system includes a medication station and a controller responsive to patient admittance status information. The medication station includes at least one securable compartment configured to hold medication. The controller is configured to assign a patient to the at least one securable compartment such that medications for the patient are able to be placed into the at least one securable compartment. The controller is also configured to selectively permit access to the medications for the patient in the at least one securable compartment when the patient admittance status information indicates the patient is currently admitted, and restrict access to retrieval of the medications for the patient in the at least one securable compartment when the patient admittance status information indicates the patient is not currently admitted.

19 Claims, 8 Drawing Sheets

(56) References Cited

U.S. PATENT DOCUMENTS

| | | | | |
|---|---|---|---|---|
| 8,126,590 | B2* | 2/2012 | Vahlberg | G06Q 10/087 700/237 |
| 8,131,397 | B2* | 3/2012 | Vahlberg | G06Q 10/087 700/236 |
| 8,140,186 | B2* | 3/2012 | Vahlberg | G06Q 10/087 700/240 |
| 8,239,062 | B2* | 8/2012 | Vahlberg | G06Q 10/087 700/236 |
| 2001/0002448 | A1* | 5/2001 | Wilson et al. | 700/233 |
| 2003/0120384 | A1* | 6/2003 | Haitin | A61G 12/001 700/242 |
| 2004/0054436 | A1* | 3/2004 | Haitin | A61G 12/001 700/236 |
| 2006/0125356 | A1 | 6/2006 | Meek, Jr. et al. | |
| 2006/0149416 | A1* | 7/2006 | Mohapatra et al. | 700/242 |
| 2007/0088461 | A1* | 4/2007 | Haitin | A61G 12/001 700/241 |

OTHER PUBLICATIONS

Chinese Fifth Office Action for Application No. 200880025543.1, dated Jun. 2, 2015, 16 pages.
Notification of Third Office Action received from the Chinese Patent Office dated Nov. 13, 2014.
Canadian Office Action in Canadian Patent Application No. 2690417, dated Oct. 2, 2014, 3 pages.
Japanese Office Action in Japanese Patent Application No. 2010-0519252, dated Dec. 4, 2012, 11 pages including English translation.
First Chinese Office Action in Chinese Patent Application No. 200880025543.1, dated Jun. 9, 2011, 7 pages including English translation.
Second Chinese Office Action in Chinese Patent Application No. 200880025543.1, dated Mar. 26, 2012, 7 pages including English translation.
Decision of Rejection in Chinese Patent Application No. 200880025543.1, dated Aug. 29, 2012, 8 including English translation.
Communication pursuant to Article 94(3) EPC in European Patent Application No. 08827052.5, dated May 17, 2010, 7 pages.
Communication pursuant to Article 94(3) EPC in European Patent Application No. 08827052.5, dated Dec. 22, 2010, 6 pages.
Examiner's First Report on Australian Patent Application No. 2008284059, dated May 25, 2012, 2 pages.
Notice of Acceptance in Australian Patent Application No. 2008284059, dated Mar. 18, 2013, 1 page.
Examination Report in New Zealand Patent Application No. 581788, dated Jun. 27, 2011, 2 pages.
Examination Report in New Zealand Patent Application No. 581788, dated Apr. 4, 2012, 2 pages.
Russian Official Action in Russian Patent Application No. 2010107606, dated Apr. 12, 2012, 10 pages including English translation.
Fourth Office Action in Chinese Application No. 200880025543.1, dated Feb. 16, 2015, 10 pages.
Chinese Decision of Rejection for Application No. 200880025543.1, dated Feb. 5, 2016, 6 pages excluding translation.
Canadian Office Action for Application No. 2690417, dated Oct. 14, 2015, 4 pages.
Chinese Sixth Office Action for Application No. 200880025543.1, dated Sep. 14, 2015, 7 pages.
Canadian Office Action for Application No. 2690417, dated Oct. 6, 2016, 5 pages.

* cited by examiner

PATIENT-SPECIFIC MEDICATION DISPENSING AND NOTIFICATION SYSTEM

STATEMENT AS TO RIGHTS TO INVENTIONS MADE UNDER FEDERALLY SPONSORED RESEARCH OR DEVELOPMENT

Not Applicable.

FIELD

The present disclosure generally relates to apparatus and methods for providing health care and, in particular, relates to providing care to a patient through controlled access to medication.

BACKGROUND

It is well known in the medical community, and in particular, in hospitals, to provide centrally located medication and supply dispensing stations, such as wall cabinets, manually secured patient cassette drawers, and automated dispensing machines. Such generally accessible stations serve several functions including the distribution of medicines and supplies to patients. These stations work well for their intended purpose. However, there are disadvantages to such centralized stations. One disadvantage is that after a patient is discharged, the medications are frequently not retrieved from the station, and consequently remain in the station. These easily accessible medications are often either stolen or mixed in the station with medications for other patients.

SUMMARY

Embodiments of the patient-specific medication dispensing and notification system disclosed herein provide patient-specific dispensing of medications with patient-specific notifications to the caretaker responsible for the dispensing of the medications.

According to one embodiment of the present disclosure, a medication dispensing system comprises a medication station and a controller responsive to patient admittance status information. The medication station comprises at least one securable compartment configured to hold medication. The controller is configured to assign a patient to the securable compartment such that medications for the patient are able to be placed into the securable compartment. The controller is also configured to selectively permit access to the medications for the patient in the securable compartment when the patient admittance status information indicates the patient is currently admitted, and restrict access to retrieval of the medications for the patient in the securable compartment when the patient admittance status information indicates the patient is not currently admitted.

According to one aspect of the present disclosure, a method, for patient-specific medication dispensing and notification, comprises the following: receiving an admit-discharge-transfer (ADT) alert, evaluating a list of patients whose medications are stored in a medication station to determine if the list includes the patient for whom the ADT alert was received, and transmitting a notification to adjust medications for the patient in response to the ADT alert received for the patient, if the list of patients treated by the medication station includes the patient for whom the ADT alert was received.

According to another embodiment of the present disclosure, a computer-readable medium having computer-executable instructions for causing a processor to execute instructions to control a medication station by performing steps comprising receiving admittance status information for the patient, and assigning the patient to at least one securable compartment of a medication station, such that at least one medication for the patient is able to be placed into the securable compartment. The computer-readable medium also comprises computer-executable instructions for performing steps comprising selectively permitting access to the medication in the securable compartment when the admittance status information indicates the patient is currently admitted, and restricting access to retrieve the medication in the securable compartment when the admittance status information indicates the patient is not currently admitted.

Additional features and advantages of the invention will be set forth in the description below, and in part will be apparent from the description, or may be learned by practice of the invention. The objectives and other advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the discussed embodiments as claimed.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

In the following detailed description, numerous specific details are set forth to provide a full understanding of the present disclosure. It will be obvious, however, to one ordinarily skilled in the art that the embodiments of the present disclosure may be practiced without some of these specific details. In other instances, well-known structures and techniques have not been shown in detail not to obscure the disclosure.

Figure 1:
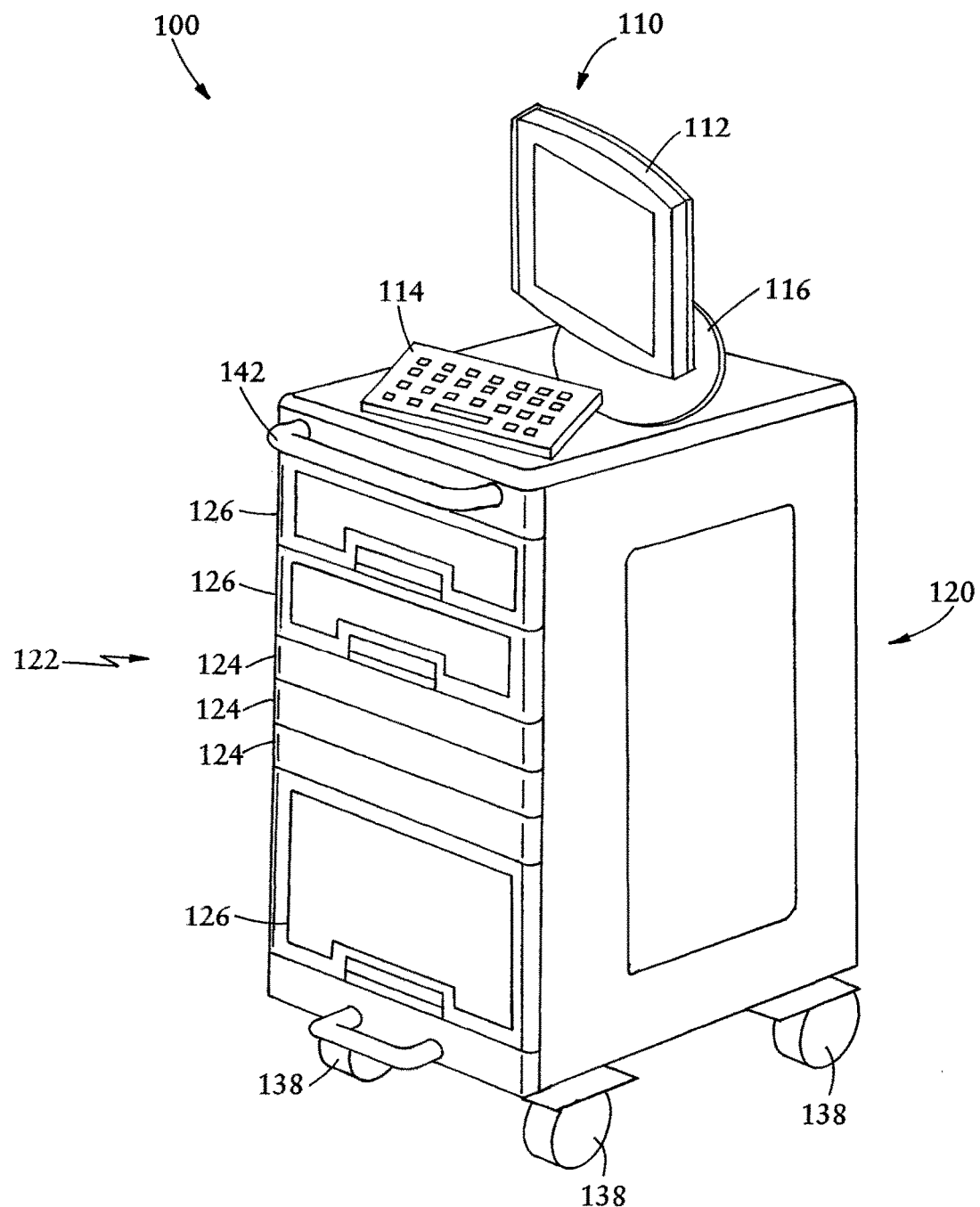
FIG. 1 illustrates an automated dispensing machine (ADM) for patient-specific medication dispensing and notification according to one embodiment.

Referring now to the drawings, FIG. 1 illustrates an ADM 100 according to certain embodiments.

The ADM 100 is a patient-specific medication dispensing and notification system configured to provide patient-specific dispensing of medications with patient-specific notifications regarding the medications for the patient. The ADM 100 is a type of medication dispensing system. The ADM 100, through its electronic interface 110, allows authorized users, such as caregivers, to access medications securely stored in the station 100, while restricting access to unauthorized users. Furthermore, when a patient that will be or is assigned to the ADM is admitted to or removed from the facility in which the ADM 100 is used, the ADM 100 transmits an alert to either add or remove medications for the patient. Consequently, the ADM helps prevent the disappearance of medications for patients, such as after they are discharged, or mixing of medications between different current patients.

The ADM comprises a cabinet 120 and the electronic interface 110. The cabinet 120 includes a plurality of modular storage compartments, here shown as drawers 122. The number and type of drawers 122 used can be custom configured within the cabinet 120 to match the medication and supply needs of the facility using the ADM 100. In the illustrated embodiment, there are two types of drawers 122: supply drawers 126 for use in holding general supplies and medical drawers 124 for use in holding medical supplies, such as medicine. The medical drawers 124 are securable. In certain embodiments, the supply drawers 126 can also be securable. The secured medical drawers 124 are electronically controlled, while the supply drawers 126 are manually controlled. For example, a person can open and close a manually controlled supply drawer 126 with little or no preliminary requirements such as providing a password or code. Manually controlled drawers can either be accessed (i.e., opened and closed) by hand with no impediments, similar to conventional storage drawers, or alternatively can be made accessible through a first securing arrangement, while electronically controlled drawers are accessible through a second securing arrangement.

Figure 2:
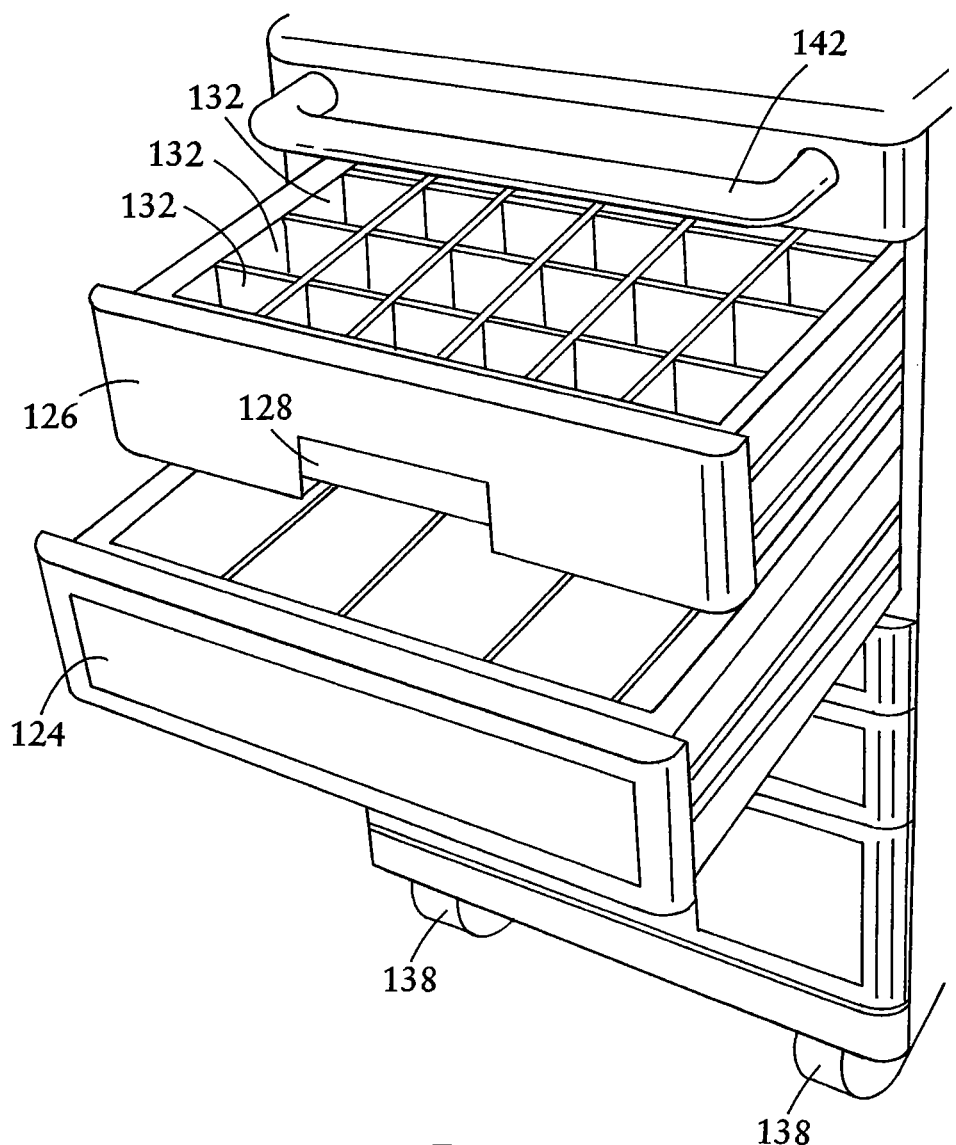
FIG. 2 is a perspective view of the ADM of FIG. 1 with drawers extended.
Figure 3:
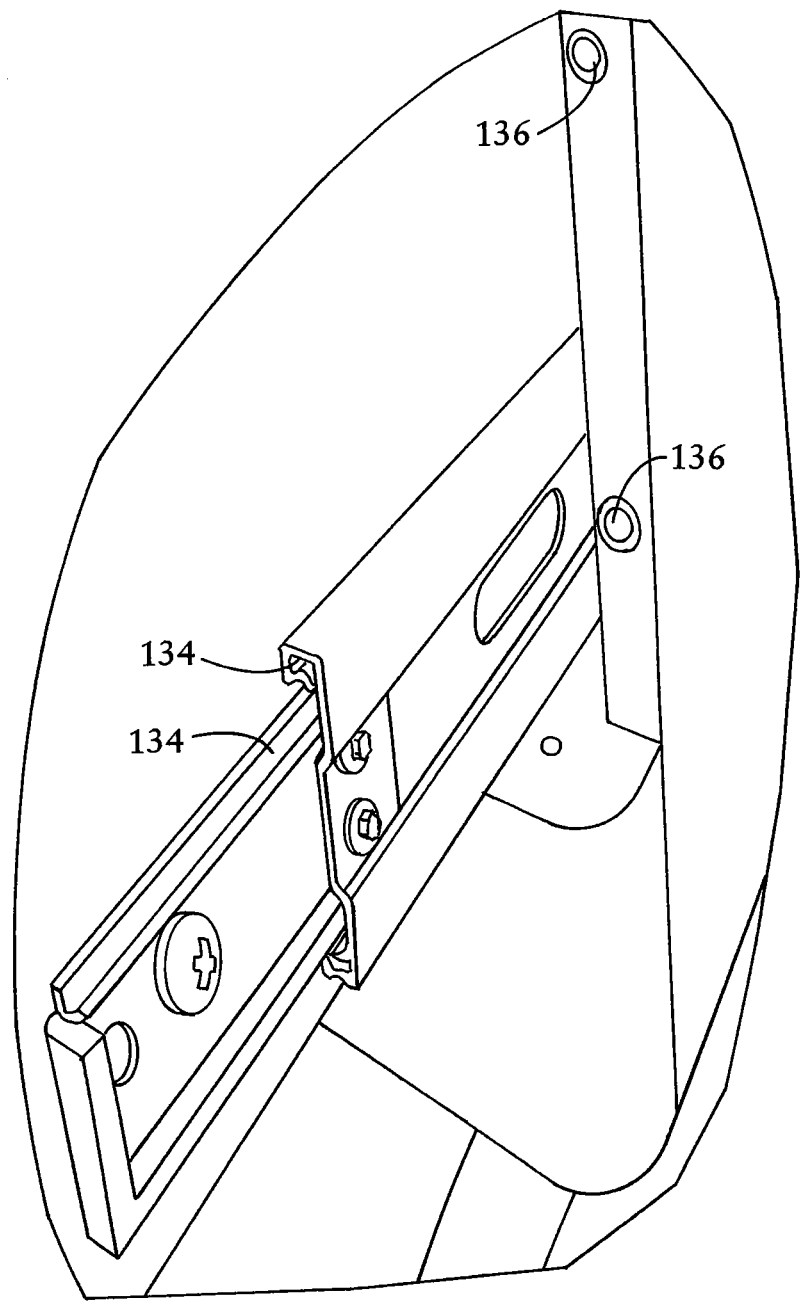
FIG. 3 is a perspective view of the ADM of FIG. 1 showing the cabinet drawer rail.

FIGS. 2-3 illustrate a typical configuration of drawers 122 for the ADM 100. The drawers 122 are matrix drawers, which are drawers divided into equally accessible compartments by adjustable or fixed dividers 132. The number and type of dividers 132 used can be custom configured within each drawer 122 to match the medication and supply needs of the facility using the station 100.

In certain embodiments, the configuration of drawers 122 can be similar to the drawer configuration found in the presently commercially available product known as a MedStation automated medication management system from Cardinal Health, Inc., Dublin, Ohio. A MedStation system can be configured with different kinds of drawers 122 that include drawers with CUBIE receptacles, matrix drawers of different heights, and MiniDrawers™. CUBIE, Matrix and Double Deep Matrix are terms understood by those skilled in the art. CUBIE receptacles, drawers 122, and related dispensing machines are fully disclosed in U.S. Pat. Nos. 6,116,461 and 6,338,007, which are incorporated herein by reference. There can also be patient-specific CUBIE receptacles that contain multiple medications and supplies for a single patient.

Supply drawers 126 have handles 128, whereas medical drawers 124 do not. In certain embodiments, either type of drawer 126 or 128 can have handles 128. The securable medical drawers 124 automatically open a relatively short distance, e.g., less than two inches, from the cabinet 120 when they are electronically unlocked. This may be accomplished by spring-loaded solenoids. Supply drawers 126 need to be manually opened and do not automatically open when unlocked. In certain embodiments, the supply drawers 126 automatically open as well. The particular drawer 122 design can be any chosen design with sound engineering judgment. In the illustrated embodiment 100, the drawer design 122 includes rails 134, as illustrated in FIG. 3, that slidably connect the drawers 122 to the cabinet 120 in a well-known manner. Indicators 136 are used in indicating if a drawer 122 is unlocked. In certain embodiments, indicators 136 can be used to indicate if the drawer 122 contains desired supplies. In the illustrated embodiment, the indicators 136 include an indicator light 136 mounted on a front surface of the cabinet 120, as shown, so that it can be easily observed when a drawer 122 is open. Alternatively, the indicator lights 136 could be on the drawers 122. The electronic interface 110 could also provide an appropriate indication.

The ADM 100 is movable in certain embodiments. Returning to FIG. 1, the ADM 100 has at least a first ground-engaging wheel 138 (an embodiment with four wheels is shown), and at least a first handle 142 for use in transporting the ADM 100. In certain embodiments, other means of movement may be used. In certain embodiments, depending on the location and type of electronic interface 110, the cabinet 120 can also have a top work surface which can vary in size and shape.

In certain embodiments, the cabinet ADM 100 can include an illumination light inside the handle 142 for illuminating the drawers 122. In this way, an opened drawer's 122 contents are illuminated obliquely. This illumination light may be positioned in the cabinet handle 142 or attached to the underside of the handle 142. The illumination light is turned on when a drawer 122 is opened. The drawers 122 could also incorporate translucent bins and gentle illumination from below to silhouette the drawer 122 contents.

Figure 4:
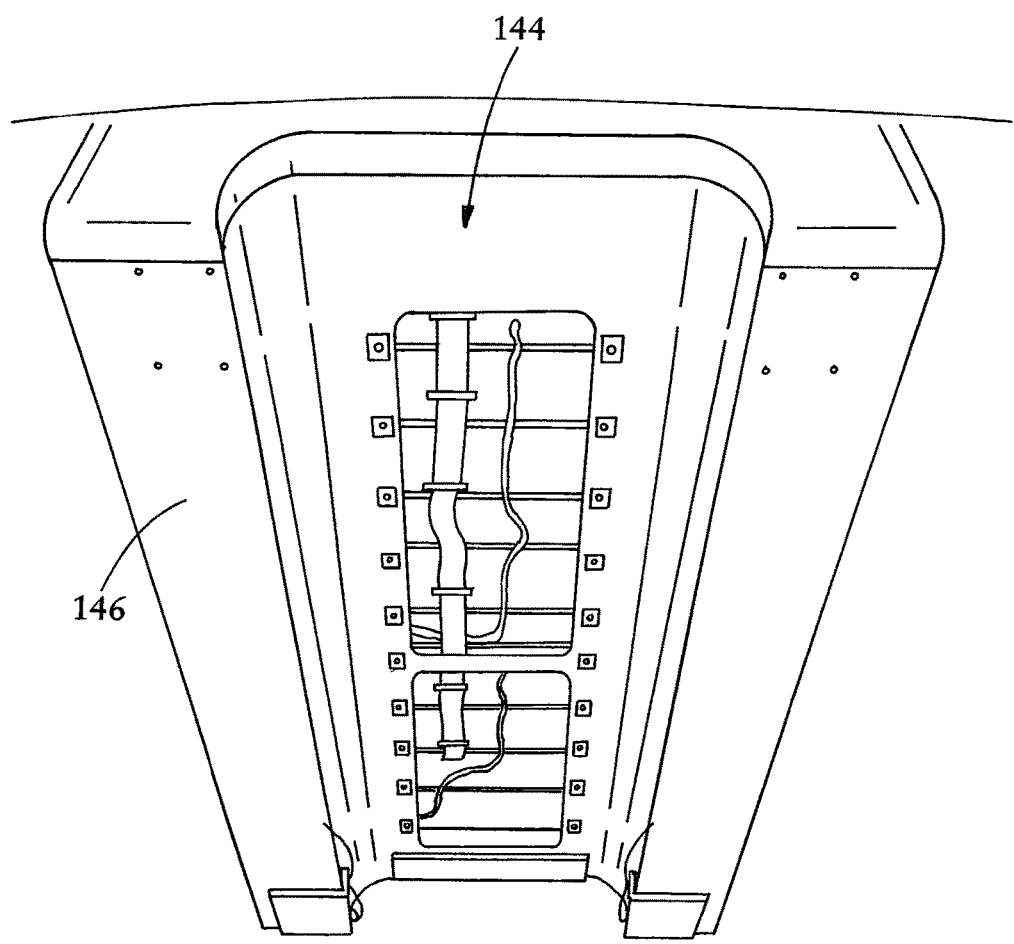
FIG. 4 is a top perspective view of the back of the cabinet of the ADM of FIG. 1.

FIG. 4 is a top perspective view of the back of the cabinet 120 of the ADM of FIG. 1. As noted above, secured drawers are electronically controlled. In case there is a loss of power to the ADM 100, and/or some electrical computer malfunction prevents normal access to the drawers 122, the cabinet 120 can be equipped with a manual release mechanism for use in unlocking the drawers 122. An access system 144 is provided so that a manual release mechanism can be accessed. At least one of the cabinet back panels 146 provides the required access system 144. This gives access to each drawer's 122 manual release mechanism.

Figure 5:
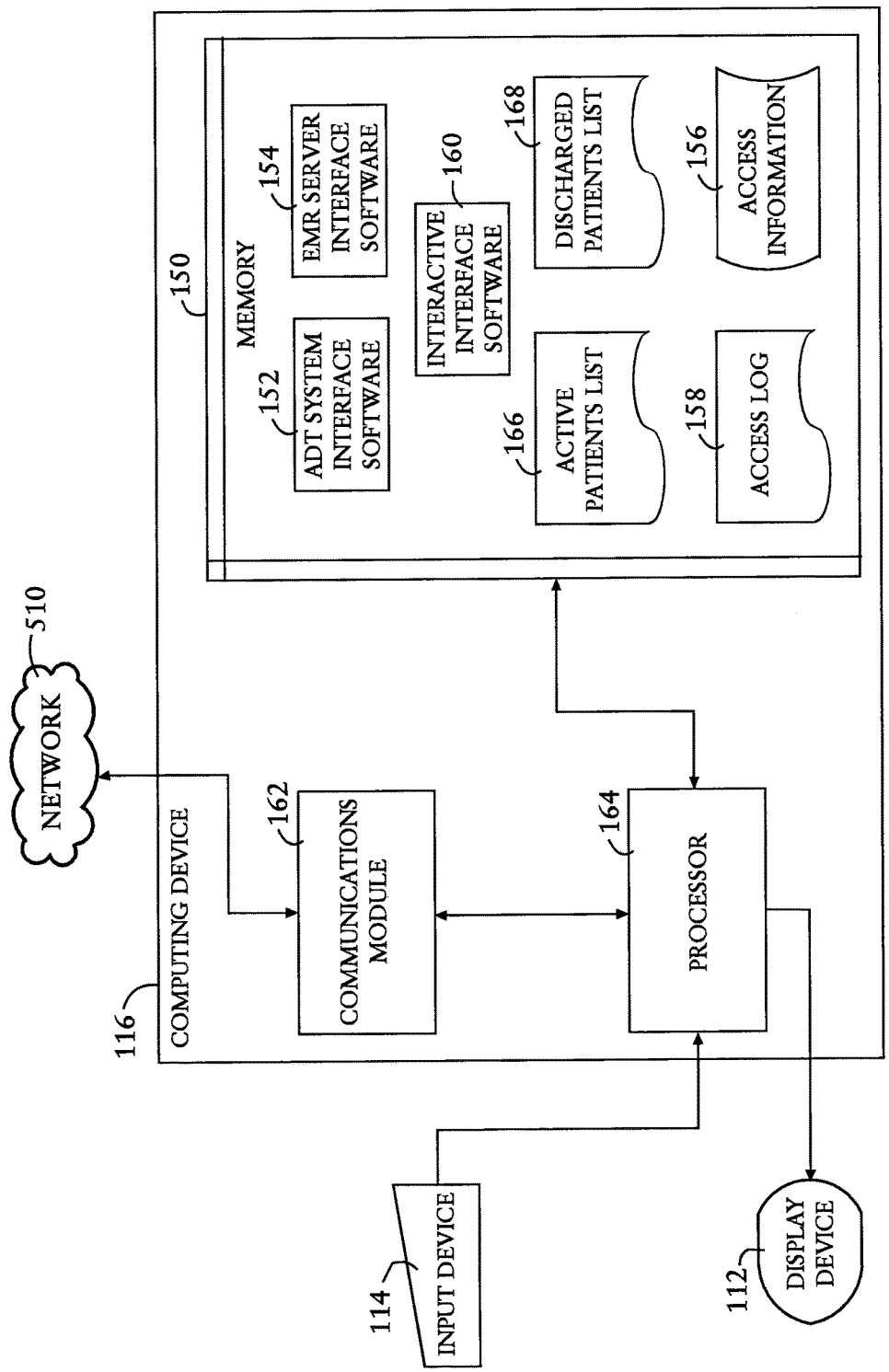
FIG. 5 is a block diagram of the electronic interface of the ADM of FIG. 1.

FIG. 5 is a block diagram of the electronic interface 110 of the ADM 100 of FIG. 1. The electronic interface 110 comprises a computing device 116, display device 112 and an input device 114.

The display device 112 is a flat panel display in the exemplary embodiment. In certain other embodiments, the display screen 112 can be a cathode ray tube (CRT) display, vacuum fluorescent display (VFD), light emitting diode (LED) display, plasma display panel (PDP), liquid crystal display (LCD), organic light emitting diode (OLED), or surface-conduction electron-emitter display (SED). The input device 114 is a keyboard. In certain embodiments, the input device 114 can be a keypad integral with the cabinet, touch-screen input, mouse, or a microphone. For example, in embodiments without a physical keyboard, the input device 114 can be a virtual keyboard. The virtual keyboard automatically appears on the display 112 when the system detects a type-in field. The virtual keyboard is a feature that hospital staffs appreciate even more than the physical keyboards because it minimizes the number of objects in the room and also decreases the risk of infection and contamination.

The computing device 116 comprises a processor 164, communications module 162, and memory 150. The processor 164, for example, a central processing unit (CPU), drives software stored in the computing device's memory 150 or elsewhere.

The communications module 162 provides networking capability in order to connect to a network 510, which is described in further detail below. Networking capability is achieved via a communication layer that enables data transmissions. Networking can be achieved by the use or the installation of data cables from the ADM 100 to a central network device for the network 510, such as a router or switch, or by using a wireless connection. An alternate technology would use existing phone cabling of the facility to transport data, thus avoiding the cost and deadlines associated with the installation of new cabling.

Stored in the memory 150 is software 152 for interfacing with an admit-discharge-transfer (ADT) system, software 154 for interfacing with an electronic medical record (EMR) server, interactive interface software 160, access information 156, an access log 156, and a list of active patients 166, and a list of discharged (or inactive) patients 168. The memory 150 can include volatile and/or non-volatile sections.

The interactive interface software 160 is used in interacting with a user of the ADM 100, as discussed in further detail below with reference to FIG. 8. The interactive interface software 160 maintains at least a list of patients 166 being treated whose items are stored in the corresponding ADM 100 ("active patient list"), and, in certain embodiments, the software can maintain a separate list of patients 168 who were previously being treated and whose items were stored in the ADM 100, but who are no longer active ("discharged patient list"). Both lists 166 and 168 are stored and maintained in memory 150 by the interactive interface software 160. The interactive interface software 160 references access information 156 stored in memory 150 when authenticating a caregiver attempting to use the ADM 100 through the interactive interface software 160. The interactive interface software 160 communicates with and accesses information from the ADT system interface software 152 and the electronic medical record (EMR) interface software 154, discussed below. In certain embodiments, the interactive interface software 160 is configured to run on any ADM with physical features similar to the features of the ADM(s) 100 discussed herein, in order to provide other ADMs with the interactive software functionality of the ADM(s) discussed herein. For example, the interactive interface software 160 is configured to run on the Medstation discussed above, as well as the ADM disclosed in U.S. patent application Ser. No. 10/810,379, entitled "POINT OF CARE STATION," filed on Mar. 26, 2004, which is hereby incorporated by reference in its entirety for all purposes.

The ADT system interface software 152 is configured to receive and interpret alerts received from an ADT system. ADT system alerts, which are patient specific, include admission alerts, discharge alerts, and transfer alerts. In certain embodiments, the ADT system interface software 152 is configured to receive and interpret alerts containing admit, discharge, transfer, or other patient admittance status information from any system. The EMR interface software 154 is configured to access, read, and write information on a device storing EMRs. In certain embodiments, the ADT system interface software 152 and the EMR interface software 154 are standardized using standards available from Health Level Seven, Inc. (HL7), so that the ADM 100 can be used with any facility network. In certain embodiments, the ADM 100 contains software to interface with nearly every major system vendor using proprietary or non-proprietary interfaces. The interactive interface software 160 is configured to broadcast or otherwise transmit admit, discharge, and transfer notifications in response to the ADT alerts interpreted by the ADT system interface software 152.

The electronic interface 110 uses the interactive interface software 160 to control access to items stored in the cabinet 120. In order to access the items, special access must first be granted. Two levels of access to the ADM 100 software systems are supported. Before medication can be dispensed, the caregiver must log in with access information. One method is to have the caregiver enter a username and password, or just a password in order to gain access to the items stored in the drawers 122. Another method is to have the caregiver use a swipecard authenticated with either password or fingerprint. The ADM 100 can be used with cards with a magnetic strip or chip, proximity cards or chips that the caregiver would carry, and the like. The ADM 100 may also require a password and ID entry in order to gain access to the items stored in the compartments 28. The interactive interface software 160 can also start a time-out to log off and lock supply drawers 126 in response to closing a drawer 122.

In certain embodiments, the electronic interface 110 can be in a remote location with respect to the ADM 100. Consequently, in certain embodiments, an ADM as disclosed herein does not include an electronic interface. An ADM without an electronic interface, can, for example, include an input for connecting to an electronic interface with similar features to the electronic interface 110 disclosed herein, such as through a physical connection/port, or through a wireless connection.

The caregiver interacts with the ADM 100 through the electronic interface 110. If the electronic interface 110 has been idle for a predetermined time, such as three minutes, the system will automatically log off. In certain embodiments, other predetermined amounts of time can be used. To log back on at the same point in the ADM interface software 160, the access information is re-entered. If the same access information for the same caregiver is entered, the caregiver's location in the interactive interface software 160 is preserved. If access information for a different caregiver is entered, the initial screen for the interactive interface software 160 will be displayed. In certain embodiments, there is no automatic log off. In certain embodiments, the ADM 100 displays a fast log out button to allow caregivers to interrupt their session and leave the room momentarily, and secures the system.

To access items within the drawers 122, while a caregiver is logged on, any one of the authorized drawers 122 can be opened depending on a patient's admittance status. In another embodiment, while a caregiver is logged on, one or more of authorized supply drawers 126 can be opened.

In embodiments where tracking of items is included, the needed item can be retrieved and recorded on-screen. This mode of interaction works best for caregivers with a clear mental picture of where items are in the cabinet 120, or who can quickly recognize an item on sight. This mode also allows items to be accessed and recorded while the interactive interface software 160 is in mid-operation on another task. In another embodiment, the display 112 provides a screen interface for each drawer 122. This interface may illustrate any and all the items and their locations in drawer 122 sections. This may be shown graphically with pictures or a list of items and their locations. This may help the caregiver to intuitively direct their attention to relevant items. If the caregiver takes nothing from the drawer, the on screen menu for that drawer 122 will persist (even if the drawer 122 has been shut again) until the caregiver presses the "none taken" button or goes to the next screen if another drawer 122 is opened. If the caregiver has taken an item(s) and has recorded what the caregiver has taken on the touch screen, the menu will disappear when the caregiver shuts the drawer 122. In another embodiment, an "out of stock" button can be provided beside each item button to inform restockers about items that need more urgent attention—for example, a nurse needed a particular item but the item was not there. In yet another embodiment, a "dispatch" button could be provided to prompt a restocker to come to the room immediately with a refill.

In certain embodiments, the ADM 100 may allow caregivers to inform the system when a particular item has run out and needs to be restocked. At least three alternate policies for use of this interface 160 are possible: (1) a button is pressed any time anybody notices a depleted item; (2) a button is pressed when lack of an item has inconvenienced a caregiver; (3) a button serves as a panic button to request a restocker to immediately bring a set of new stock for that ADM 100.

In certain embodiments, the memory 150 further includes a bedside information gateway (BIG). BIG is an application-independent system that allows easy and efficient access to mission-critical applications directly from the ADM 100. It makes it possible for medical staff to leverage applications throughout the facility regardless of the technology (Web or Windows) used for these applications. BIG makes it possible for physicians and nurses to access quickly and easily a wide variety of medical applications and information, therefore shortening the time it takes the caregiver to make rounds. Whether used to consult a patient file, access laboratory/radiology results or prescriptive applications, the ADM 100 acts as a window on the applications inside the hospital mainframe, such as by using the network 510. With the BIG technology, only the purchase of verification software is required to implement verification.

The electronic interface 110 can be located on or in the cabinet 120. The electronic interface 110 can be removably or permanently attached to the cabinet 120. In certain embodiments, portions of the electronic interface 110 can be attached to the cabinet 120 via an arm, such as an articulated arm.

Figure 6:
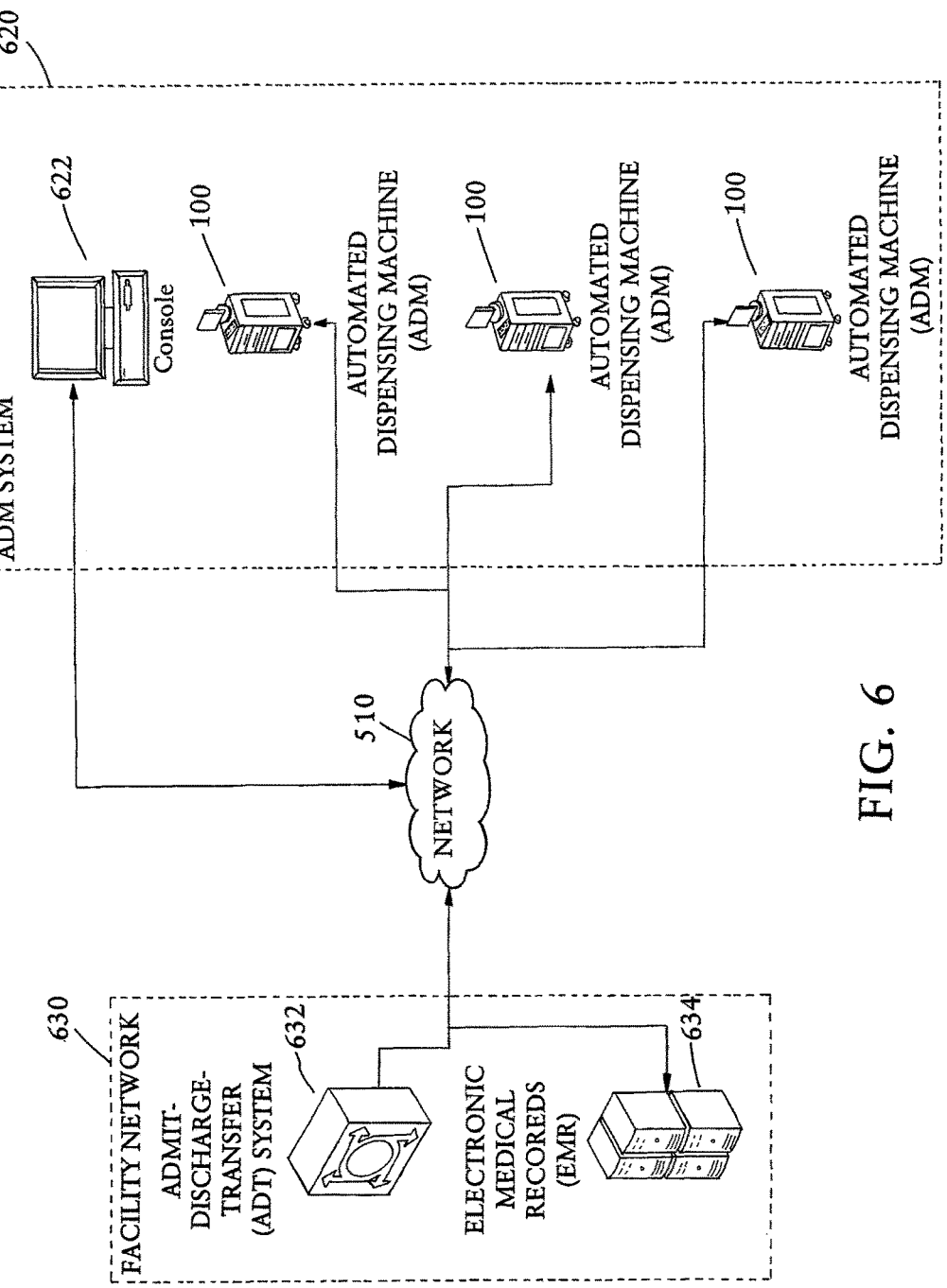
FIG. 6 is a block diagram of a network configuration for the ADM of FIG. 1.

FIG. 6 is a block diagram of a network configuration for the ADM of FIG. 1. A plurality of ADMs 100 are connected to a facility network 510 through their respective communication modules 162. Also connected to the network is a console device 622, such as a computer. The console device 622 can be located in a pharmacy so it is easily accessible to an individual, such as a pharmacist, responsible for dispensing medications to an ADM 100. The console device 622 and the ADMs 100 together form the ADM system 620 of the network 510. The other portion of the network 510 is the facility network 630, which includes an ADT system 632 and a networked server storing EMRs 634. Each ADM 100 of the network 510 thus has access to admission/discharge/transfer information for a patient, a patient's medical record, and possibly any other medical application or information.

The ADT system 632 broadcasts alerts for a patient, including alerts that a patient has been admitted to, discharged, or transferred from the facility. For example, if a patient John Doe is admitted to a hospital that uses an ADT system 632, the ADT system 632 would broadcast an alert over the network 510 that patient John Doe has been admitted. The alert would be received by an ADM 100 also connected to the network 510, as illustrated, which then processes the information that patient John Doe has been admitted to the hospital. The ADM 100 can then transmit a corresponding notification through the network 510 to the console 622.

The EMR server 634 stores electronic medical record information, and makes the information available over the network 510 according to appropriate security features and requirements. EMR information can include, for example, notes from patient medical history, family history, complaints, office visits, staff observations, lab tests, X-rays, prescription and drug allergy information, social history, and diagnoses.

Figure 7:
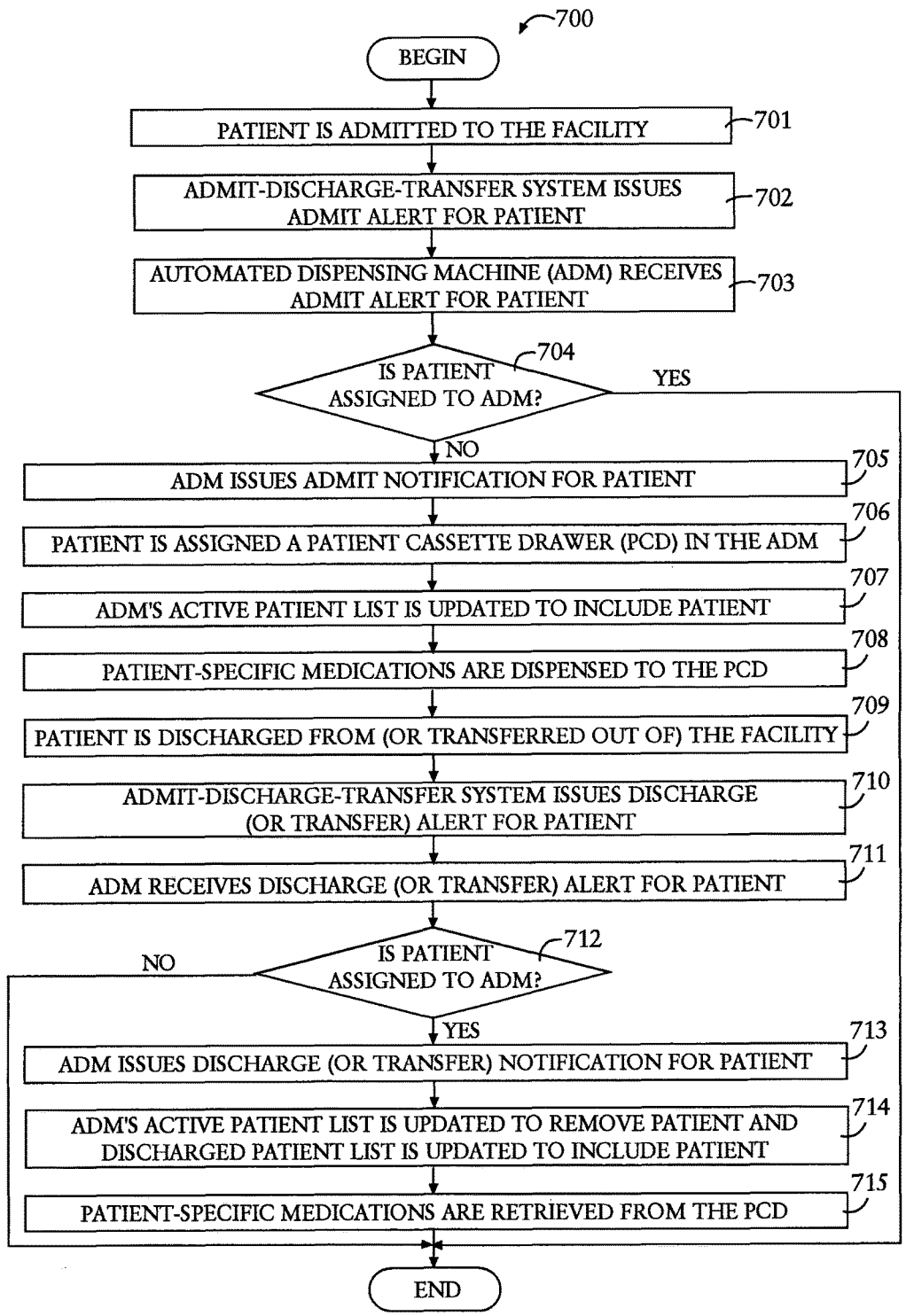
FIG. 7 is a flow diagram illustrating a process for treating a patient using the ADM of FIG. 1.

FIG. 7 is a flow diagram illustrating a process 700 for managing medications for a patient using the ADM of FIG. 1. The process 700 begins in state 701 when the patient is admitted into the facility. The ADT system 632 issues an admit alert over the network 510 in state 702 that the patient has been admitted. The electronic interface 110 of the ADM 100 receives the admit alert in state 703, and, in response, determines in state 704 if the patient is already assigned to the ADM 100. For example, the interactive interface software 160 of the ADM 100 can determine whether the patient is present in the ADM's list of active patients 166. If the patient is determined to be already assigned to the ADM 100, the process 700 is completed. If, however, the patient is determined not to be assigned to the ADM 100, the process proceeds to state 705. In certain embodiments, state 704 determines if the patient is assigned to any ADM 100 on the network 510.

In state 705, the ADM 100 sends its own admit notification for the patient. The ADM's admit notification is broadcast to devices within the ADM system 620 on the network 510, including the console 622. The admit notification can be broadcast according to any method known in the art, including, but not limited to, automated telephone call, automated voicemail, Short Message Service (SMS) message, Enhanced Messaging Service (EMS) message, Wireless Application Protocol (WAP) push, instant message, email, RSS feed, screen alert, and page.

The admit alert received at the console 522 notifies the console's user, such as a pharmacist, that the patient has been admitted to the hospital. In response, the pharmacist accesses the patient's medical records from the EMR server 634 on the network 510 in order to obtain the patient's medical history, which includes the patient's prescription information. In state 706, the pharmacist (or other caregiver) assigns to the patient a patient cassette drawer (PCD) 124, or compartment(s) in the PCD 124, in the appropriate ADM 100. The appropriate ADM 100 can be selected based on the patient's location in the facility, for example. In certain embodiments, a patient can be assigned multiple PCDs 124. In certain embodiments, a patient can be assigned to a portion of a drawer 124, such as to a compartment in the drawer 124. After being assigned the patient in state 706, the ADM 100 updates its list of active patients 166 in state 707 to include the patient. In certain embodiments, the ADM 100 updates its list of active patients in response to receiving the admit alert from the ADT system 532 in state 703 or after the determination is made in state 704. An ADM 100 can be selected to house the patient's medications based on its proximity to the patient or to the relevant nurse station. The PCD assignment is made through the ADM's interactive interface software 160, such as by entering access information or entering/selecting the appropriate patient information, and then selecting a PCD 124 to assign to the patient. The pharmacist or other caregiver can then dispense the appropriate medications to the PCD 124 in state 708, which is discussed in further detail below with reference to FIG. 8.

When the patient is later discharged out of, transferred from, or otherwise leaves the hospital in state 709, the ADT system 632 issues a discharge (or transfer) alert for the patient in state 710. The ADM 100 receives the discharge alert in state 711, and, in response, determines if the patient is assigned to the ADM 100 in state 712. For example, the interactive interface software 160 of the ADM 100 can determine whether the patient is present in the ADM's list of active patients 166. If the patient is determined not to be assigned to the ADM 100, the process 700 is completed. If, however, the patient is determined to be assigned to the ADM 100, such as by being listed in the list of active patients 166 for the ADM 100, the process proceeds to state 713. In certain embodiments, state 712 determines if the patient is assigned to any ADM 100 on the network 510.

If the discharged patient is determined to be an active patient of the ADM in state 712, then in state 713, the ADM 100 sends its own discharge notification for the patient. The electronic interface 110 otherwise ignores discharge alerts received for patients not assigned to the ADM 100. The ADM's discharge notification is broadcast to devices within the ADM system 620, including the console 622. For example, the discharge notification from the ADM 100 is sent to the pharmacist console 622, and can include information to notify the pharmacist to retrieve medications for the discharged patient from the patient's assigned PCD.

Upon receiving the discharge alert at the console 622, the pharmacist in state 714 removes the patient's name from the ADM's active patient list 166, and, in certain embodiments, adds the patient's name to the ADM's inactive patient list 168. In certain embodiments, this name removal/addition is performed automatically by the ADM 100 in response to receiving the discharge alert from the ADT system 632 in state 711 or after the determination made in state 712. The addition of the patient's name to the ADM's inactive patient list 168 causes the ADM 100 to restrict access to the PCD 124 previously assigned to that patient. The pharmacist or other authorized caregiver can then retrieve the patient's medications from the appropriate PCD 124 in the ADM 100 in state 715, such as after being notified by a discharge notification sent by the ADM 100, as discussed above. Unauthorized users or caregivers will not be able to access the PCD 124 for the discharged patient, even if previously authorized.

Figure 8:
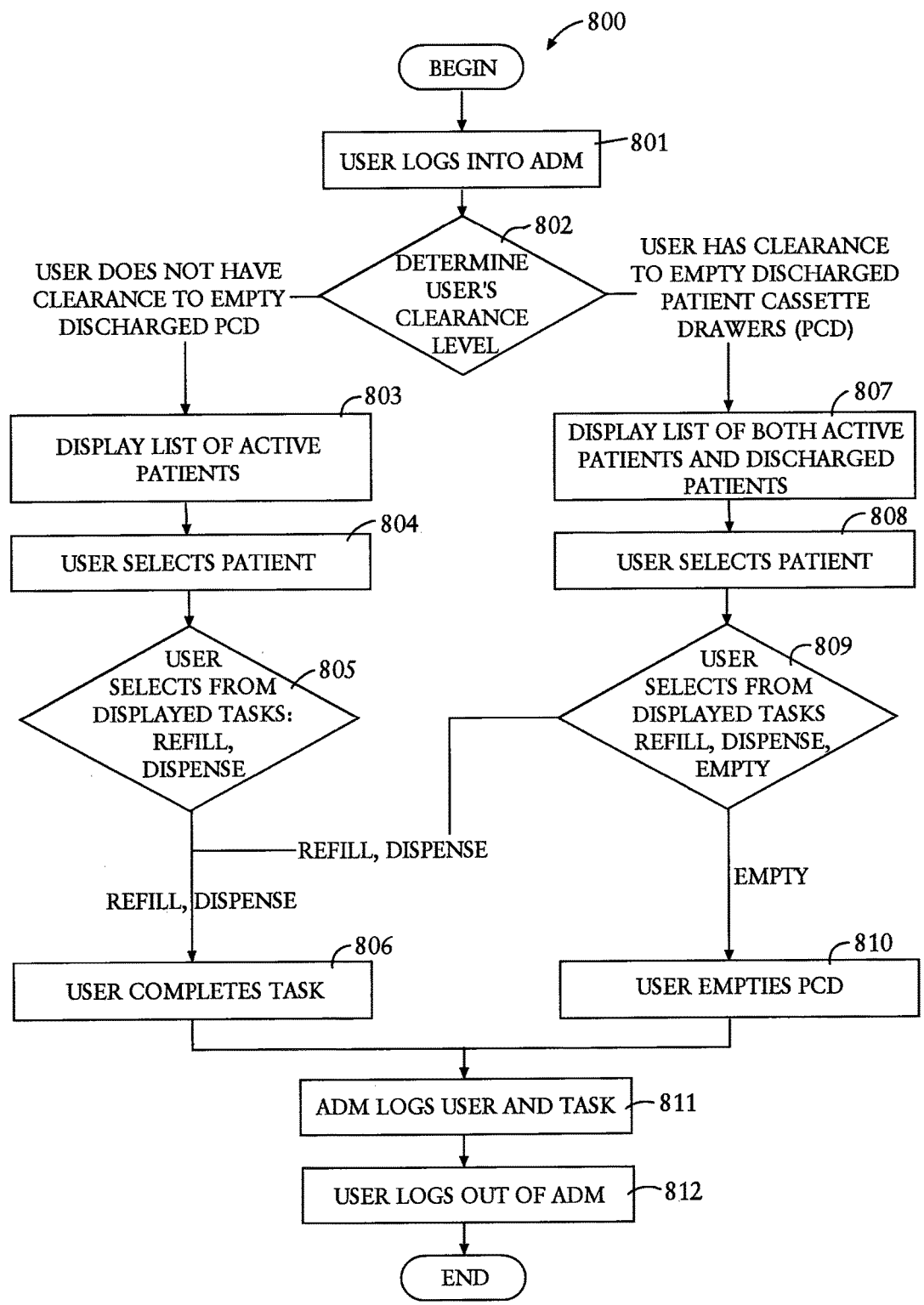
FIG. 8 is a flow diagram illustrating a process for interacting with interactive interface software of the ADM of FIG. 1.

FIG. 8 is a flow diagram illustrating a process 800 for interacting with interface software of the ADM of FIG. 1. Although FIG. 8 illustrates an embodiment where authorized users can have different levels of clearance, in other embodiments, all authorized users can have the same level of clearance.

The process 800 of interaction begins in state 801 when the caregiver logs into the ADM's interactive interface software 160. As discussed above, access to the ADM 100 is granted to the caregiver after the appropriate access information is entered, according to the access information 156 stored in the device's memory 150. After the caregiver successfully logs in, the interactive interface software 160 determines the caregiver's clearance level in state 802 using the stored access information 156. In the illustrated embodiment, a caregiver can have at least two different clearance levels: a first clearance level which does not have access to empty a discharged patient's cassette drawer, such as for a nurse, and a second, higher clearance level which does have access to empty a discharged patient's cassette drawer, such as for a pharmacist. In embodiments where an authorized user can have only one level of clearance, the process would automatically proceed from state 801 to state 807.

If in state 802 the caregiver is determined to have the first clearance level, the process moves to state 803, where a list of active patients 166 is displayed. The caregiver then selects an active patient from the active patient list in state 804. In certain embodiments, if the patient is assigned to multiple drawers 124, the interactive interface software 160 can prompt the caregiver to select a drawer 124. Next, in state 805, the caregiver is given the option of either refilling the selected patient's cassette drawer 124, or dispensing medications from the selected patient's cassette drawer 124. The interactive interface software then provides to the caregiver access to the appropriate secured patient cassette drawer 124, such as by electronically unlocking the drawer, so that the caregiver can complete the task of either refilling or dispensing in state 806.

If, however, in state 802 the caregiver is determined to have the second, higher clearance level, the process moves to state 807, where both a list of active patients 166 and a list of inactive patients 168 is displayed. The caregiver in state 808 can select either an active patient from the active patient list 166, or an inactive patient from the inactive patient list 168. In certain embodiments, if the patient is assigned to multiple drawers, the interactive interface software 160 can prompt the caregiver to select a drawer 124. Next, in state 809 the caregiver is given the option of either refilling or dispensing medications from an active selected patient's cassette drawer 124, or emptying medications from an inactive selected patient's cassette drawer 124. If the caregiver selects to either refill or dispense medications for an active patient, the process moves to state 806, as discussed above. If the caregiver selects to empty an inactive patient's cassette drawer 124, the interactive interface software 160 provides to the caregiver access to the appropriate secured discharged patient cassette drawer 124, such as by electronically unlocking the drawer, so that the caregiver can complete the task of emptying in state 810. Thus, only a caregiver with an appropriate access level has access to medications in a discharged patient's cassette drawer 124, while a caregiver without the appropriate access level cannot access the medications in the discharged patient's cassette drawer 124. A caregiver may have been notified to log in to the interface software of the ADM to empty an inactive patient's cassette drawer 124 by receiving a notification at the pharmacist console, as discussed above.

After the caregiver's task is completed in either state 806 or 810, the system records to an access log the caregiver's identification, the task performed by the caregiver, and the time the caregiver performed the task. In certain embodiments, other information can be logged, such as the dispensing, refilling, or emptying of medications.

In certain embodiments, the interactive interface software 160 of the ADM 100 is configured to track the movement of medications contained in the cabinet 120, such as when a medication is loaded and removed, to whom the medication is assigned, and which PCD 124 the medication is assigned to and/or located. These features can be achieved by adding additional tracking functionality to the interactive interface software 160, such as by expanding states 806 and 810 in the process 800 of FIG. 8 to include prompting the caregiver for information regarding the medications refilled or dispensed (in state 806) or emptied (in state 810).

As illustrated above, the ADM 100 may be integrated into a larger, perhaps care facility(ies) wide, system for controlling supplies and medicines. For one example, the ADM 100 can complement at least two other devices known as the Pyxis MedStation and the Pyxis SupplyStation units. In one recommended use, high use and patient-specific medications are stored in the ADM 100 while the MedStation unit maintains first dose and controlled medications. Slower moving drugs can be placed in the MedStation unit while the fast moving medications can be placed within the cabinet 120 of the ADM 100. The MedStation and SupplyStation units can be used to manage bulk items while the ADM 100 can manage patient-specific medications and supplies. It should be noted that the interactive interface software 160 of the ADM 100 can be configured to interface with the MedStation units.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A medication dispensing system comprising:
a mobile medication station comprising at least one securable compartment configured to hold medication and a display device; and
a controller, coupled to the mobile medication station, which is updated with patient admittance status information and responsive to the patient admittance status information, the controller configured to:
receive and interpret a broadcast message configured for simultaneous transmission to a plurality of controllers, the broadcast message comprising the patient admittance status information for a patient;
update, based on the patient admittance status information, a list of active patients whose medications are stored in the mobile medication station and a list of discharged patients whose medications are stored in the mobile medication station and who are no longer active patients;
assign the patient to the at least one securable compartment such that medications for the patient are placed into the at least one securable compartment;
selectively permit access to the medications for the patient in the at least one securable compartment when the patient is an active patient;
when the patient is a discharged patient, restrict access to retrieval of the medications for the patient in the at least one securable compartment; and
when a user logs into the medication dispensing system, the controller is further configured to:
determine a clearance level for the user;
display in the display device the list of active patients when the user has a first clearance level;
display in the display device the list of active patients and the list of discharged patients when the user has a second clearance level higher than the first clearance level;
receive a patient selection and a task selection from the user, wherein the task selection comprises one of a refill medication, a dispense medication, or an empty medication when the selected patient is a discharged patient; and
log the user and a completed, selected task, when the task is completed.

2. The system of claim 1, wherein the broadcast message comprises an admit-discharge-transfer (ADT) alert, wherein the ADT alert comprises the patient admittance status information.

3. The system of claim 1, wherein the controller comprises a display and an input device.

4. The system of claim 1, wherein the at least one securable compartment comprises a securable drawer.

5. The system of claim 3, wherein the input device comprises at least one item selected from the group consisting of a magnetic card reader, a biometric reader-sensor, a proximity reader, a radio frequency identification reader, a keyboard, symbology reader, a bar code reader, and a touch-screen monitor.

6. The system of claim 1, wherein the controller is further configured to log access to the at least one securable compartment.

7. The system of claim 1, wherein the controller is further configured to catalog the medications for the patient located in the at least one securable compartment.

8. A method, for patient-specific medication dispensing and notification, comprising:
receiving by a mobile medication station, an admit-discharge-transfer (ADT) alert configured for simultaneous transmission to a plurality of medication stations, the mobile medication station comprising a display device;
updating, based on the received ADT alert, a list of active patients whose medications are stored in the mobile medication station and a list of discharged patients whose medications were stored in the mobile medication station and who are no longer active patients;
when the ADT alert indicates that the patient is a discharged patient:
restricting access to retrieve medications in the medication station according to a clearance level to empty a patient's securable compartment, and
when a user logs into a medication dispensing system via the mobile medication station, the method further comprises:
determining a clearance level for the user;
displaying in the display device the list of active patients when the user has a first clearance level;
displaying in the display device the list of active patients and the list of discharged patients when the user has a second clearance level higher than the first clearance level;
receiving a patient selection and task selection from the user, wherein the task selection comprises one of a refill medication, a dispense medication, or an empty medication when the selected patient is a discharged patient; and
logging the user and a completed, selected task, when the task is completed.

9. The method of claim 8, wherein the ADT alert comprises a discharge alert, the method further comprising removing the patient from the list of patients if the list of patients treated by the medication station includes the patient for whom the discharge alert was received.

10. The method of claim 9, further comprising unassigning the patient from at least one securable compartment previously assigned to the patient.

11. The method of claim 8, wherein the ADT alert comprises an admit alert, the method further comprising:
adding the patient to the list of patients if the list of patients treated by the medication station does not include the patient for whom the admit alert was received; and
wherein the notification to adjust medications comprises a notification to add medications for the patient to the medication station.

12. The method of claim 11, further comprising assigning at least one securable compartment to the patient.

13. The method of claim 8, wherein the notification to adjust medications is transmitted to a pharmacist console.

14. A computer-readable medium having computer-executable instructions for causing a processor to execute instructions to control a medication station by performing steps comprising:
receiving and interpreting, by a mobile medication station, the mobile medication station comprising a display device, a broadcast admit-discharge-transfer (ADT) alert configured for simultaneous transmission to a plurality of medication stations, the broadcast ADT alert comprising admittance status information for a patient;
updating, based on the patient admittance status information, a list of active patients whose medications are stored in the mobile medication station, and a list of discharged patients whose medications were stored in the mobile medication station and who are no longer active patients;
assigning the patient to at least one securable compartment of the mobile medication station, such that at least one medication for the patient is placed into the at least one securable compartment;
selectively permitting access to the at least one medication in the at least one securable compartment when the patient is an active patient;
when the patient is a discharged patient, restricting access to retrieve the at least one medication in the at least one securable compartment; and
and
when a user logs into a medication dispensing system via the mobile medication station:
determining a clearance level for the user;
displaying in the display device the list of active patients when the user has a first clearance level;
displaying in the display device the list of active patients and the list of discharged patients when the user has an second clearance level higher than the first clearance level;
receiving a patient selection and a task selection from the user, wherein the task selection comprises one of a refill medication, a dispense medication, or an empty medication when the selected patient is a discharged patient; and
logging the user and a completed, selected task, when the task is completed.

15. The computer-readable medium of claim 14, having further computer-executable instructions for performing the step of logging access to the at least one securable compartment.

16. The computer-readable medium of claim 14, having further computer-executable instructions for performing the step of cataloging the medications for the patient located in the at least one securable compartment.

17. The computer-readable medium of claim 14, having further computer-executable instructions for performing the step of unassigning the patient from a patient cassette drawer (PCD) previously assigned to the patient.

18. The computer-readable medium of claim 14, having further computer-executable instructions for performing the step of transmitting to a pharmacist console a notification to adjust a medication for the patient.

19. The computer-readable medium of claim 14, having further computer-executable instructions for performing the step of transmitting a notification to retrieve medications for the patient when the admittance status information indicates the patient is not currently admitted.

* * * * *